(12) United States Patent
Sogaro

(10) Patent No.: US 8,690,024 B2
(45) Date of Patent: Apr. 8, 2014

(54) SPRAY CAN COMPRISING A DISCHARGE TUBE

(75) Inventor: Alberto C. Sogaro, Kronberg (DE)

(73) Assignee: Dispensys AG (CH)

( * ) Notice: Subject to any disclaimer, the term of this patent is extended or adjusted under 35 U.S.C. 154(b) by 300 days.

(21) Appl. No.: 12/680,861

(22) PCT Filed: Sep. 29, 2008

(86) PCT No.: PCT/DE2008/001610
§ 371 (c)(1),
(2), (4) Date: Jun. 9, 2010

(87) PCT Pub. No.: WO2009/043342
PCT Pub. Date: Apr. 9, 2009

(65) Prior Publication Data
US 2010/0288797 A1 Nov. 18, 2010

(30) Foreign Application Priority Data
Oct. 2, 2007 (DE) .................... 20 2007 013 747 U

(51) Int. Cl.
*B65D 83/00* (2006.01)

(52) U.S. Cl.
USPC ....................... 222/402.1; 222/562

(58) Field of Classification Search
USPC ............. 222/402.1, 526, 567–570, 499, 222/519–538
See application file for complete search history.

(56) References Cited

U.S. PATENT DOCUMENTS

| | | | | |
|---|---|---|---|---|
| 3,148,806 A | * | 9/1964 | Meshberg | 222/402.11 |
| 3,273,610 A | * | 9/1966 | Frost | 141/353 |
| 3,395,838 A | * | 8/1968 | Beres et al. | 222/402.14 |
| 3,567,081 A | * | 3/1971 | Meshberg | 222/402.17 |
| 4,775,081 A | * | 10/1988 | Morane | 222/402.13 |
| 6,783,037 B1 | | 8/2004 | Bonham | |
| 6,824,025 B1 | * | 11/2004 | Ruble et al. | 222/527 |
| 6,883,688 B1 | * | 4/2005 | Stern et al. | 222/402.1 |
| 7,025,232 B2 | * | 4/2006 | Green | 222/321.7 |
| 7,070,072 B2 | * | 7/2006 | Bonham | 222/530 |
| 7,261,103 B2 | * | 8/2007 | Katz | 128/200.15 |
| 2002/0053579 A1 | * | 5/2002 | Baumgart et al. | 222/527 |

FOREIGN PATENT DOCUMENTS

| | | | |
|---|---|---|---|
| CH | 378 802 A | 6/1964 | |
| DE | 805 203 A | 12/1958 | |
| DE | 23 38 800 A1 | 2/1975 | |
| DE | 20 2006 012416 U1 | 3/2010 | |
| EP | 1 088 772 A | 4/2001 | |
| GB | 2252132 | * 7/1992 | 222/402.1 |
| JP | 07 285585 A | 10/1995 | |
| WO | 2006/105923 A | 10/2006 | |
| WO | 2007/009282 A | 1/2007 | |

OTHER PUBLICATIONS

International Search Report corresponding to PCT/DE2008/001610 under date of mailing of Feb. 19, 2009.

* cited by examiner

*Primary Examiner* — Lien Ngo
(74) *Attorney, Agent, or Firm* — Quarles & Brady LLP

(57) ABSTRACT

The invention relates to a spray can comprising a can member (12) for holding a material that is to be sprayed, and a spray head (14) which is plugged onto a can valve located on the top face of the can member (12) and is fitted with a discharge tube (24). The spray can has an adapter which connects the spray head (14) to the discharge tube. The discharge tube (22) is connected to the adapter (16) by means of a plug-on and/or screwed connection.

11 Claims, 4 Drawing Sheets

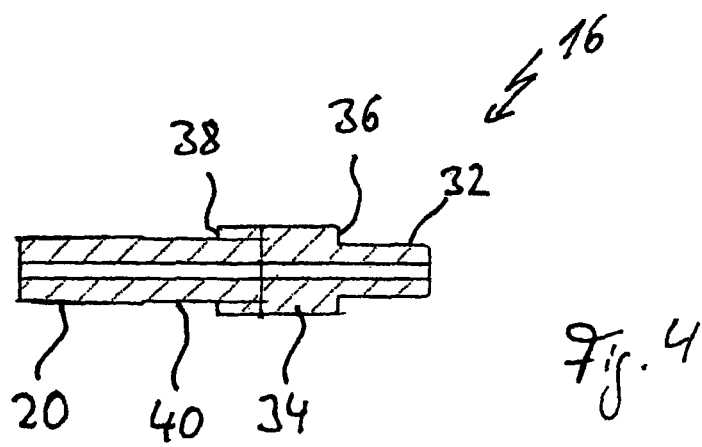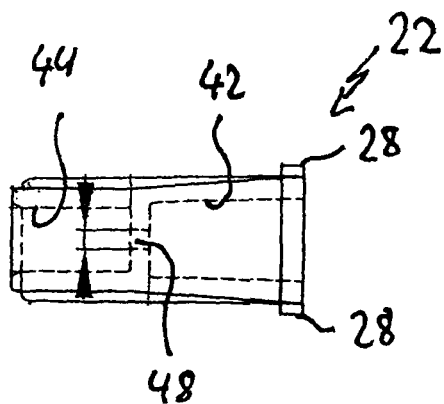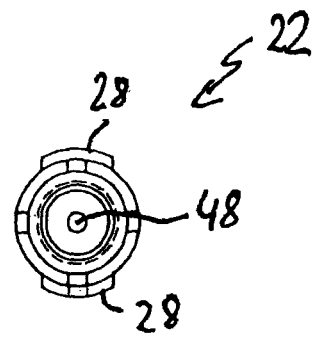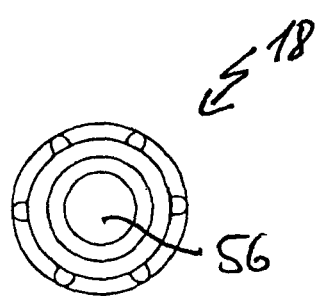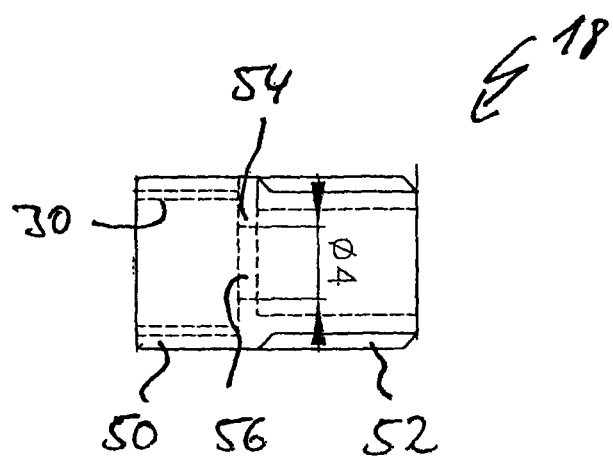

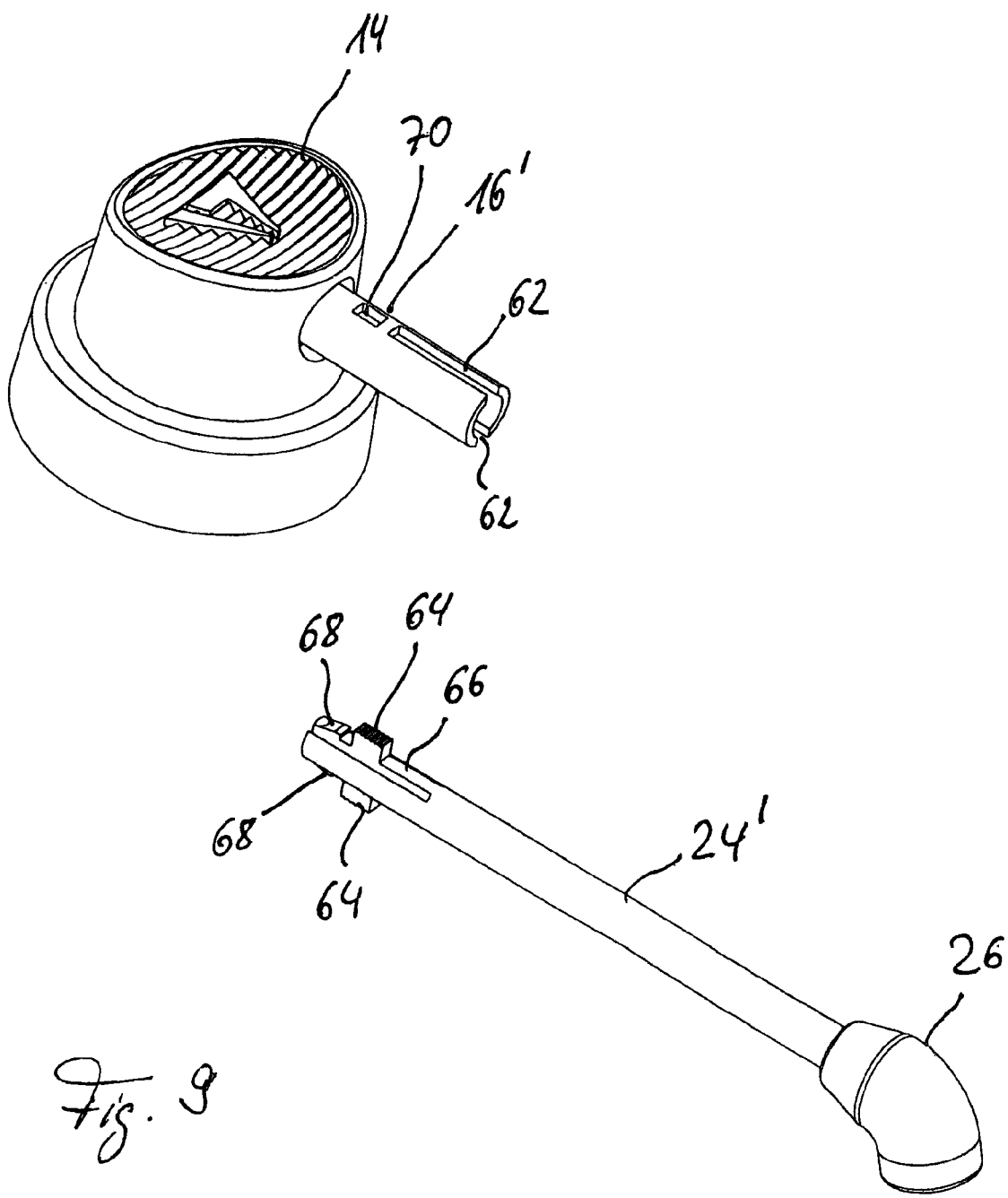

SPRAY CAN COMPRISING A DISCHARGE TUBE

CROSS-REFERENCE TO RELATED APPLICATIONS

This application claims priority to PCT International Application No. PCT/DE08/001,610 filed on Sep. 29, 2008, which claims priority to German Application No. 20 2007 013 747.8 filed on Oct. 2, 2007, both of which are fully incorporated by referenced herein.

The invention relates to an aerosol spray can comprising a can body for holding a substance that is to be sprayed, and a spray head plug-mounted on a can valve topping the can body and is fitted with a delivery tube.

One such aerosol can is known to be in use for delivering and aerosolizing liquid pharmaceutical products. The can or container features a delivery and/or metering member which may be a valve. This aerosol can is employed especially for oral application of a pharmaceutical product. It comprises a spray head mounted on the metering valve and is provided with a tubular section for mounting an end portion of a delivery tube via a rotatable connector. The delivery tube is mounted on the tubular section such that the right-angled delivery tube can be rotated on the tubular section to orient the delivery tube as required.

The drawback of this known aerosol can is that changing the delivery tube is only possible with a lot of exertion, risking its damage. Changing the delivery tube is, however, a mandatory requirement for proper hygiene.

The invention has thus the object of providing an aerosol can comprising a spray head featuring a delivery tube which can now be simply changed with little exertion.

This object is achieved in accordance with the invention by the aerosol spray can as featured in claim 1.

Consequently, an aerosol spray can in accordance with the invention is proposed comprising a can body for holding a substance that is to be sprayed, and a spray head plug-mounted on a can valve topping the can body and is fitted with a delivery tube. An adapter is provided which connects the spray head to the delivery tube which is connected to the adapter by means of a non-destructing releasable plug and/or screw-threaded connector.

This design of an aerosol can in accordance with the invention now makes it possible to simply change the delivery tube so that, for example, the same aerosol can can now be put to use orally on several patients with a changed delivery tube always satisfying existing stringent antiseptic or hygiene requirements, simply by releasing it from the plug and/or screw-threaded connector and fitting a new delivery tube to the adapter.

The aerosol can in accordance with the invention is particularly suitable for applying a matting agent to a tooth/stump for video scanning, or an agent for dental occlusal analysis.

In one preferred embodiment of the aerosol can in accordance with the invention the connector comprises a male taper configured on the adapter or delivery tube to mate with a female taper of the delivery tube or adapter, resulting in a pressfit between the adapter and the delivery tube like a Luer-type connector.

To prevent inadvertant release of the delivery tube from the adapter when using the aerosol can, a locking device is provided in another preferred embodiment of the aerosol can in accordance with the invention, locking the delivery tube to the adapter and designed releasable to separate the delivery tube from the adapter.

For example, the locking device is a union nut located on the adapter and cooperating with a counterpart arranged on the delivery tube. More particularly, the counterpart is an end portion of the delivery tube or an element configured at the end portion of the delivery tube such as a radial tab for engaging a screw thread.

Preferably, the adapter features a circumferential slot for captive locating the union nut.

The circumferential slot may be configured so that the union nut is axially shiftable on the adapter, it being axially displaced when the union nut is released from the counterpart.

The circumferential slot may be designed wide enough so that its edge facing away from the delivery tube serves as a back stopper for the union nut when releasing the delivery tube from the adapter. Expediently, the union nut comes up against this stopper just before attaining its release position so that turning the union nut further displaces the delivery tube relative to the adapter, resulting in the pressfit between these two elements being released by the pressure exerted on the counterpart of the delivery tube, making it simple to detach the delivery tube from the adapter.

However, it is also possible, of course, that a union nut as described is provided at the delivery tube but with the delivery tube featuring a male taper and the adapter a female taper, the counterpart then being likewise configured at the adapter, for example, in the form of an annular collar comprising at least one recess to configure radially protruding tabs for engaging a screw thread of the union nut.

The end portion or counterpart may be mounted either on a tubular section or made in one piece therewith.

In another alternative embodiment of the aerosol can in accordance with the invention the delivery tube comprises at its end facing the adapter at least one latching tab engaging a latching element in a recess of the adapter.

In one simple design embodiment the latching tab is formed by axial slots in the end portion of the delivery tube.

To connect the delivery tube to the adapter precisely positioned, the delivery tube is preferably inserted into a channel of the adapter, the adapter comprising a guideway for the latching element.

To simplify releasing the delivery tube from the adapter, the latching tab in one preferred embodiment comprises a radially protruding actuator, for example, in the form of a pushbutton.

Preferably, the actuator is guided in the guideway when the delivery tube is inserted in the adapter, the actuator consequently likewise being a guide preventing the delivery tube from tilting out of place when inserted in the adapter.

The channel of the adapter into which the delivery tube is inserted may be lined with a sealant, for instance an elastomeric coating of e.g. PTE to enhance the seal of the system overall.

In yet another alternative embodiment of the aerosol can in accordance with the invention the delivery tube is fitted to the adapter by means of a sleeve as a low-cost alternative.

In still another preferred embodiment of the aerosol can in accordance with the invention the adapter is connected to the spray head by a pressfit preferably designed so that the adapter can now be pulled off of the spray head without the use of a tool, although it is just as possible to make the adapter and a housing of the spray head in one piece.

Especially when discharging a substance as an oral aerosol the delivery tube features to advantage a nozzle head at the end facing away from the spray head. The nozzle head which may be configured as usual in the practice may be mounted rotatable on the delivery tube for directing the delivery jet.

Further advantages and advantageous aspects of the subject matter of the invention read from the description and claims and as evident from the claims.

Illustrated simplified diagrammatically in the claims are two example aspects of an aerosol can in accordance with the invention as detailed in the following description, in which:

FIG. 4 is a longitudinal section through the adapter;

FIG. 5 is a side view of an end portion of the delivery tube;

FIG. 6 is a face view of the end portion;

FIG. 7 is a side view of a union nut for locking in place on the end portion;

FIG. 8 is a face view of the union nut;

FIG. 9 is an overview of a second embodiment shown exploded; and

Figure 1:
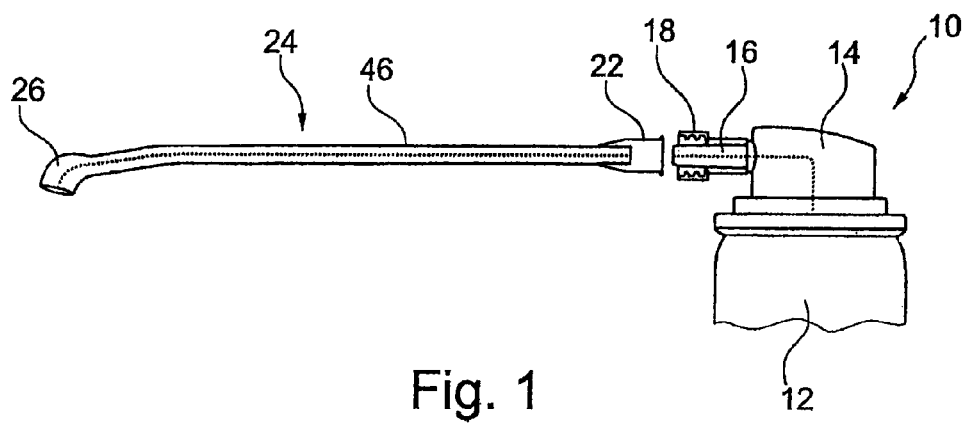
FIG. 1 is a view of an aerosol spray can featuring a spray head and an adapter/delivery tube system configured in accordance with the invention shown prior to fitting the delivery tube.

Referring now to FIGS. 1 to 8 there is illustrated an aerosol can 10 comprising a cylindrical can body 12 mounting a spray head 14 topping a can valve (not shown).

The spray head 14 which to actuate, i.e. open the can valve is pressed down in the direction of the can body 12, comprises a radially protruding adapter 16 inserted pressfitted in a radial opening of the spray head 14, shown in detail in FIG. 4.

Rotatably mounted on the adapter 16 is a union nut 18.

Figure 2:
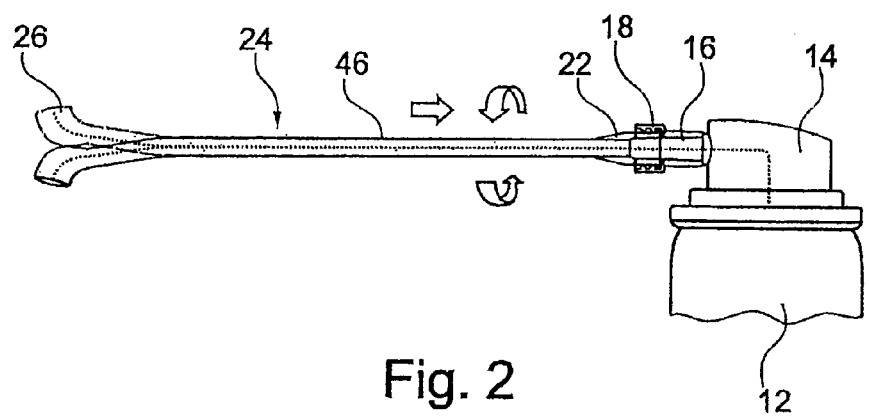
FIG. 2 is a view the same as in FIG. 1 but showing how the delivery tube is mounted on the adapter.
Figure 3:
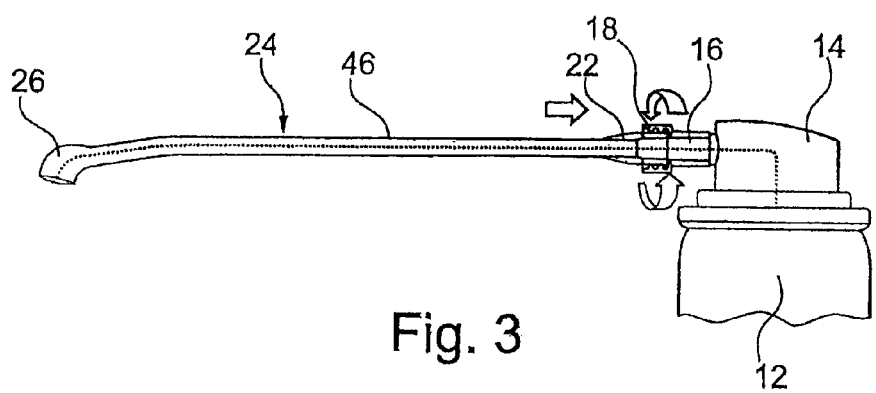
FIG. 3 is again a view the same as in FIG. 1 but showing how the delivery tube is locked on the adapter.

Referring now to FIGS. 2 and 3 there is illustrated how at its end portion 20 forming a male taper facing away from the spray head an end piece 22 of a delivery tube 24 can be fitted provided at its end facing away from the end piece 22 with a rotatably mounted nozzle head 26 which in use of the aerosol can 10 produces an aerosol of the substance to be delivered.

To lock the delivery tube on the adapter 16 the union nut 18 can be screwed onto the end piece 22 of the delivery tube 24. For this purpose the end piece 22 ends in a circumferential slot or two radially protruding tabs 28 offset from each other by 180° for cooperating with a female screw thread 30 of the union nut 18.

Referring now to FIG. 3 there is illustrated how, because the union nut is freely rotatably mounted on the adapter 16 the delivery tube can be freely turned on the adapter 16 to orient the nozzle head 26, it only being after the nozzle head 26 has been oriented as wanted that the union nut 18 is located by its female screw thread engaging the tabs 28 at the end piece 22 of the delivery tube 24.

Referring now to FIG. 4 there is illustrated a view in detail of the adapter 16 consisting of a tube with a uniform inner diameter of, for example, 1 mm comprising at one end a tapered end portion 20 and a cylindrical end portion 32 at the other end inserted by a pressfit in the corresponding opening in the spray head 14. In the middle portion of the adapter 16 an annular collar 34 is configured, forming by a face 36 a stop for the housing of the spray head 14 and a second face 38 as a stop for the union nut 18 shiftingly mounted in a waisted portion 40 which in this case has a length of approx. 5 mm.

When assembled, the end piece 22 of the delivery tube 24 is seated on the tapered end portion 20. The end piece 22 comprises a female taper corresponding to the end piece 22. The combination of female taper, male taper and union nut forms a modified Luer lock system.

Referring now to FIGS. 5 and 6 there is illustrated in detail how the end piece 22 of the delivery tube 24 comprises, as aforementioned, a female taper 42 as well as a cylindrical mount 44 at the female taper 42 facing away from the female taper, a 46 of the delivery tube 24 being inserted by a pressfit in the cylindrical mount 44. The cylindrical mount 44 and the portion of the female taper 42 are interconnected by an opening 48 of reduced diameter.

Referring now to FIGS. 7 and 8 there is illustrated in detail how at the end facing away from the cylindrical mount 44 the end piece 22 of the delivery tube 24 comprises the aforementioned radially projecting tabs 28 cooperating with the union nut 18.

The union nut 18 comprises a threaded portion 50 in which the female screw thread 30 is configured. At the end facing away from the threaded portion 50 the union nut 18 features a guide portion 52 guided on the annular collar 34 of the adapter 16.

The threaded portion 50 and guide portion 52 are spaced away from each other by a partition 54 provided with an opening 56, the edge of which guides the union nut 18 in the region of the waisted portion 40 of the adapter 16.

Figure 10:
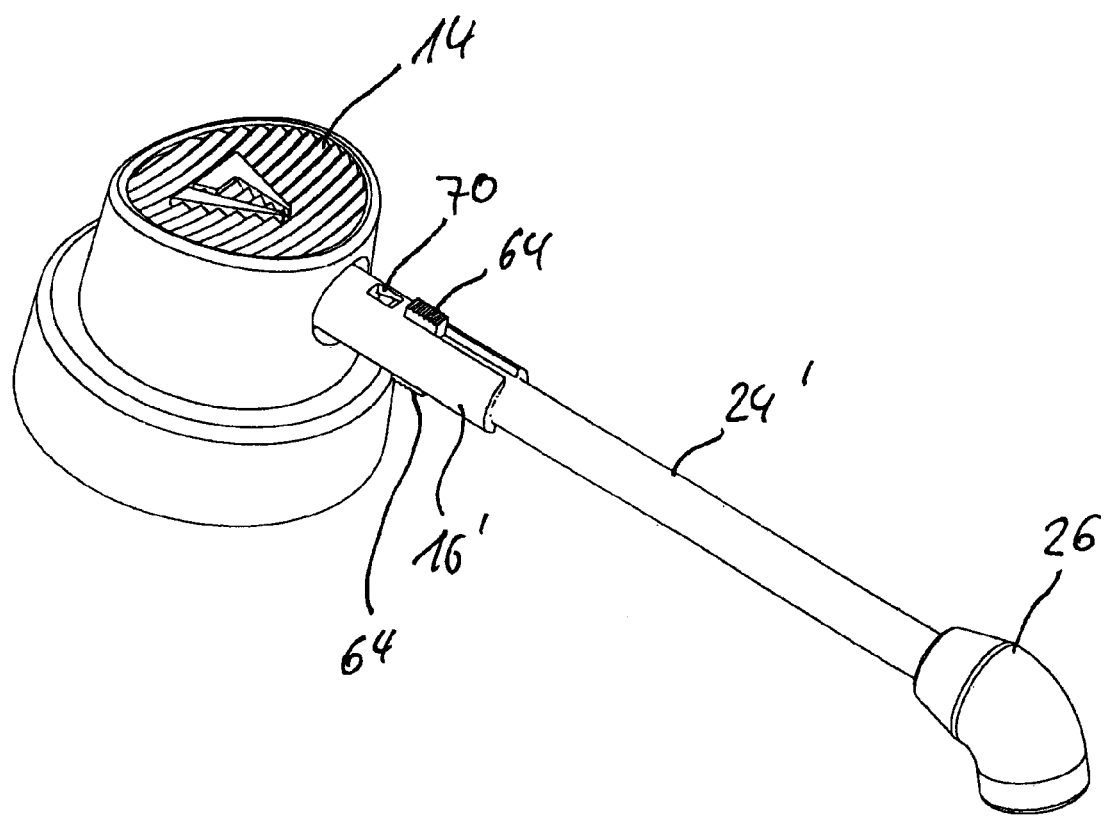
FIG. 10 is a view of the embodiment as shown in FIG. 9 but as fitted.

Referring now to FIGS. 9 and 10 there is illustrated how the aspect shown therein likewise features a spray head 14 comprising a radial opening 58 in which an adapter 16' is inserted in a pressfit.

For this purpose the adapter 16' comprises an end portion 60 of reduced diameter.

At its end facing away from the end portion 60 the tubular adapter 16' is provided with axial slots 62 offset from each other by 180° and serving as guideways for the actuator pushbuttons 64 of the end latching tabs 66 of a replaceable delivery tube 24'. The latching tabs 66 are provided by two axial slots 72 of the delivery tube 24'.

In their end portions the latching tabs 66 comprise radially protruding lugs for latching the delivery tube 24' to the adapter 16' in recesses 70 of the adapter 16'.

To release the delivery tube 24' from the adapter 16' or to change the delivery tube 24' the actuator pushbuttons 64 arranged in the slots 62 are depressed so that the latching lugs 68 of the latching tabs 66 are pressed out of the recesses 70, allowing the delivery tube 24' to be withdrawn from the adapter 16'. This enables a new, hygienic delivery tube 24' to be inserted in the adapter 16' and latched into place in the adapter 16' by the lugs.

LIST OF REFERENCE NUMERALS 10 aerosol can
12 can body
14 spray head
16 adapter
18 union nut
20 end portion
22 end piece
24 delivery tube
26 nozzle head
28 tabs
30 female screw thread
32 end portion
34 annular collar
36 face
38 face
40 circumferential slot
42 female taper
44 mount
46 tubular section 48 opening
50 threaded portion
52 guide portion
54 partition
56 opening
58 opening
60 end portion
62 slot
64 actuator pushbutton
66 latching tab
68 latching lug
70 recesses
72 slot

The invention claimed is:

1. An aerosol spray can comprising:
    a can body for holding a substance that is to be sprayed;
    a spray head plug-mounted on a can valve topping the can body;
    a delivery tube connected to the spray head by an adapter, the delivery tube being connected to the adapter by at least one of a plug and screw-threaded connector; and
    a locking device locking the delivery tube to the adapter and being releasable to separate the delivery tube from the adapter, whereby the locking device is a union nut freely rotatably mounted on the adapter and cooperating with a counterpart arranged on the delivery tube.

2. The aerosol can as set forth in claim 1, in which the connector comprises a male taper configured on the adapter or delivery tube to mate with a female taper of the delivery tube or adapter, resulting in a pressfit between the adapter and the delivery tube.

3. The aerosol can as set forth in claim 1, in which the adapter includes a circumferential slot captive locating the union nut.

4. The aerosol can as set forth in claim 3, in which the union nut is axially shiftable on the adapter in the circumferential slot.

5. The aerosol can as set forth in claim 2, in which the female taper or the male taper is made in one piece with the delivery tube.

6. The aerosol can as set forth in claim 2, in which the female taper or male taper is made at an end piece of the delivery tube.

7. The aerosol can as set forth in claim 1, in which the adapter is connected to the spray head by a pressfit.

8. The aerosol can as set forth in claim 1, in which the adapter and a housing of the spray head are made in one piece.

9. The aerosol can as set forth in claim 1, in which the delivery tube features a nozzle head at the end facing away from the spray head.

10. The aerosol can as set forth in claim 1, in which the union nut has internal threads threadably engageable with the counterpart arranged on the delivery tube.

11. An aerosol spray can comprising:
    a can body for holding a substance that is to be sprayed;
    a spray head plug-mounted on a can valve;
    a delivery tube connected to the spray head by an adapter, the delivery tube being connected to the adapter by at least one of a plug and screw-threaded connector; and
    a locking encircling at least a portion of the adapter and locking the delivery tube to the adapter, said locking device being freely rotatably fixed relative to the adapter and engaging a counterpart arranged on the delivery tube to lock the delivery tube to the adapter.

* * * * *